(12) United States Patent
Mattila et al.

(10) Patent No.: US 8,247,765 B2
(45) Date of Patent: Aug. 21, 2012

(54) METHOD FOR MEASURING GASES AND CORRESPONDING ION MOBILITY SPECTROMETER

(75) Inventors: Terhi Mattila, Kuopio (FI); Osmo Anttalainen, Mikkeli (FI); Esko Karpanoja, Mikkeli (FI); Heikki Paakkanen, Kuopio (FI); Tero Katto, Mikkeli (FI); Erkka Saukko, Tampere (FI)

(73) Assignee: Environics Oy, Mikkeli (FI)

( * ) Notice: Subject to any disclaimer, the term of this patent is extended or adjusted under 35 U.S.C. 154(b) by 131 days.

(21) Appl. No.: 12/922,263

(22) PCT Filed: Apr. 2, 2009

(86) PCT No.: PCT/FI2009/050249
§ 371 (c)(1),
(2), (4) Date: Sep. 13, 2010

(87) PCT Pub. No.: WO2009/122017
PCT Pub. Date: Oct. 8, 2009

(65) Prior Publication Data
US 2011/0006199 A1 Jan. 13, 2011

(30) Foreign Application Priority Data
Apr. 3, 2008 (FI) .................................... 20085283

(51) Int. Cl.
*H01J 49/28* (2006.01)

(52) U.S. Cl. .......................... 250/294; 250/281; 250/282
(58) Field of Classification Search .................. 250/281, 250/282, 290, 294, 298
See application file for complete search history.

(56) References Cited

U.S. PATENT DOCUMENTS
2006/0054804 A1 3/2006 Wexler
2008/0054174 A1 3/2008 Boyle et al.

FOREIGN PATENT DOCUMENTS
WO 2008008826 1/2008

*Primary Examiner* — Michael Maskell
*Assistant Examiner* — Hanway Chang
(74) *Attorney, Agent, or Firm* — Fildes & Outland, P.C.

(57) ABSTRACT

The invention relates to a method and device for measuring gaseous substances, in which the method comprises the stages:
ionization of the sample gas in a gas flow,
leading of the ionized gas flow through an elongated ion-mobility measuring chamber in the cross-section defined by it,
filtering out of ions from the ionized gas flow at a distance from the measuring electrodes, permitting the passage of only the ions travelling from the flow cross-section at the selected point,
separation of ions with a different ion mobility, with the aid of a transverse static electric field and at least one measuring-electrode pair arranged along the wall of the measuring chamber.

12 Claims, 5 Drawing Sheets

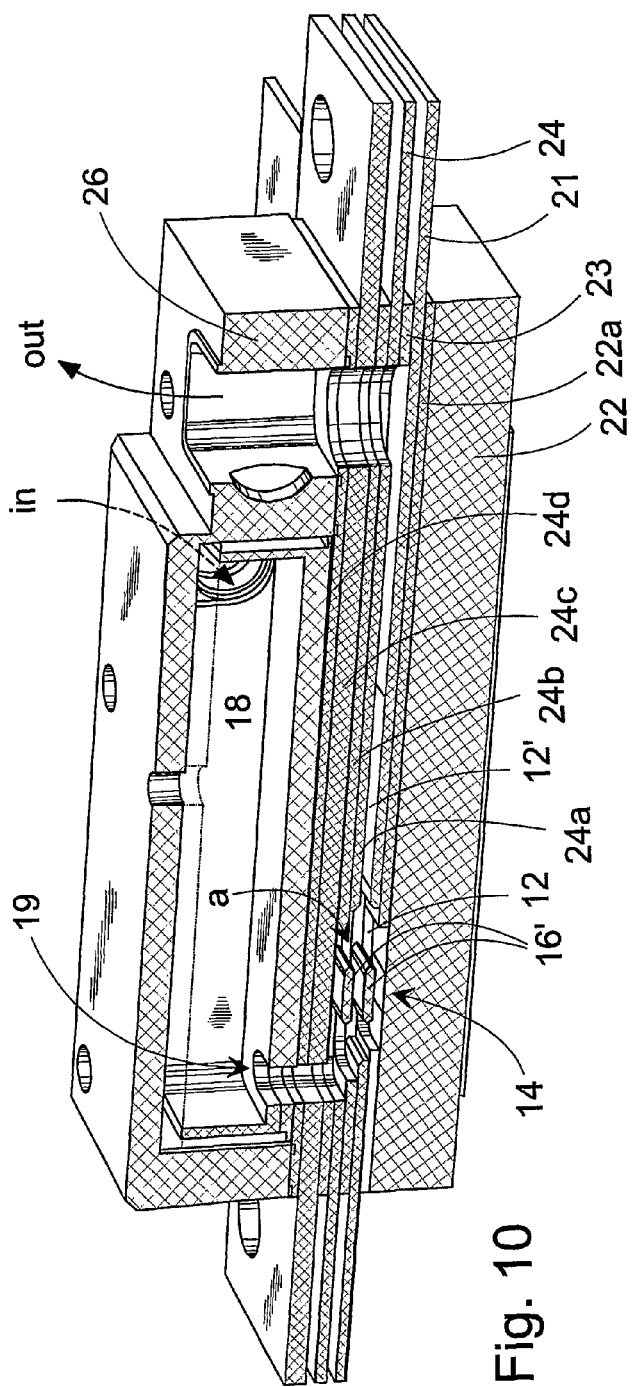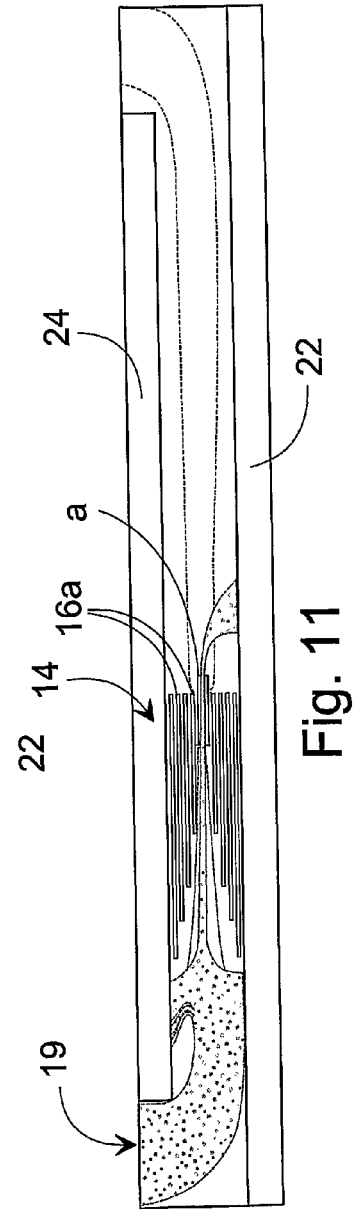

METHOD FOR MEASURING GASES AND CORRESPONDING ION MOBILITY SPECTROMETER

FIELD OF THE INVENTION

The present invention relates to a method for measuring gases, which method comprises the stages:
  ionization of the sample gas in a gas flow,
  leading of the ionized gas flow through an elongated ion-mobility measuring chamber in its defined flow cross-section,
  separation of ions with differing ion mobilities with the aid of a transverse electric field and at least one measurement-electrode pair arranged on the wall of the measuring chamber.

The invention also relates to an ion mobility spectrometer (IMS) implementing the method.

PRIOR ART

Ion mobility spectrometry (IMS) is a method for measuring gaseous impurities in air (Eiceman & Karpas, 2005). The mobility of ions is measured in many ways. The most common is time-of-flight IMS, or drift IMS. Another known method is aspiration IMS. This is used to measure the mobility of both ions and aerosol particles. Aspiration IMS is based on the fact that ions move in an air flow and most usually with an electric field that is most usually perpendicular to the flow. If the electric field is kept constant, the ions travel to different locations on the basis of their electrical mobility, the mobility being determined according to the measurement location. Measurement can also be made by changing the electric field relative to time, in which case the ions representing different mobilities are measured at different times.

Application publication US 2007/0023647 A1 (Zimmermann) discloses one ion mobility spectrometer, in which the sample gas is ionized and guided to a narrow point in the cross-section of the transport-gas flow, before the measurement electrodes. This is a matter of so-called second-order aspiration IMS. Ideally, the ionized sample gas is led to the centre of the flow cross-section of the transport gas and electric field as a narrow flow, when all the ions start from the same transverse distance relative to the consecutive electrodes. The variables affecting the lateral movement of the molecules are then the mass and charge of the molecule. The separation precision of the channels improves significantly compared to the ion flow from the entire cross-sectional area. The control of the transport gas and the sample gas to be ionized complicates the construction, however. The least disturbance in even one flow component can easily give rise to a relatively large error. A similar construction is disclosed in publication US 2006/0054804A1 (Wexler).

Publication WO 2008/008826A2 discloses several different types of IMS device. FIGS. 5 and 6 of the publication show an IMS device using a Bradbury-Nielsen multi-component gate, in which a frequency in the order of 1 Mhz is used, together with a scanning DC voltage. Such an electrode arrangement with several phased RF sources combined with DC scanning is extremely complicated.

In principle, the sample gas could be led to the centre, but practical implementation is difficult and for this reason the publication discloses a model, in which the sample gas is guided to the edge of the transport-gas flow. In terms of the parabolic velocity profile of the transport-gas flow, such a feed will not be optimal, but instead will cause imprecision.

FIG. 1 shows a traditional way of implementing an aspiration cell. The ions $J_{1-n}$ come to separate measurement strips $e_1$-$e_3$ from the entire area of the flow channel. Though most of the ions come from the centre due to the velocity profile of the flow, considerable imprecision arises, due to the ions coming from the edges of the flow. FIG. 2 shows a so-called SWEEP cell construction, in which the ions $J_{1,n}$ come to an individual measurement strip $e_1$-$e_2$ from the entire area of the flow channel. In the implementation, the separation of the ions takes place by altering the filed of the measurement strip. This method too suffers like the previous one from the broad arrival distribution of the ions.

DESCRIPTION OF THE INVENTION

The present invention is intended to create a simpler method and device than previously for measuring gas samples, particularly to implement so-called second-order aspiration IMS. The characteristic features of the method according to the invention are stated in Claim 1 and the characteristic features of the corresponding IMS device are stated in Claim 6. By means of the filtering technique according to the invention, the emission flow can be in the centre of the flow cross-section, in which the velocity profile of the flow is greatest. The construction is substantially simpler that Zimmermann's device described above. At its simplest, there can be an absolute 0 field in the emission flow, but in it too in a more highly developed embodiment the ions can be selected using a small electric field and collector electrodes, which allow only some of the ions through the emission channel to separation.

In the ion-collecting part flow, i.e. in the said shut-off channel, the electric field is static relative to the mobility of the ions. A slowly changing (less than 100 Hz, more usually 0-50 Hz) or absolutely static electric field may be used, according to the embodiment chosen. For example, In a period of one second a slowly changing electric field can be used to optimize the separation of ions with different mobility. The electric fields of the pre-filter are long enough in the direction of flow for the ions to be able to be collected out of the shut-off channel and the undisturbed operation of the emission channel ensured. After the pre-filter, the separation electrodes are located axially in the measuring chamber, according to the calculated paths.

The static electric field of the emission channel requires same-potential electrodes on both sides. However, each electrode of the static electric field can be on the opposite side of an insulating plate and be simultaneously a second electrode of the shut-off channel.

With the aid of the ion-filtering technique according to the invention, considerable measurement precision is achieved, compared to a detector without ion filtering. By means of the filtering technique according to the invention, the emission channel can be in the centre of the flow cross-section, where the velocity profile of the flow is greatest. The construction is substantially simpler than that of Zimmermann's device described above.

The sample air is ionized, for example with alpha or beta radiation. The ions are admitted to the measuring part only from a limited section. In the present invention, the ions are filtered out of the edges of the flow channel, from the so-called shut-off flow and ions are only permitted into the mobility measurement from the central part of the flow channel, from the so-called emission flow. The corresponding part channels are referred to as the shut-off channel and the emission channel. This considerably improves mobility resolution, compared to a situation, in which ions are permitted to enter the measurement from the entire area of the flow channel (so-called first-order aspiration IMS). The shut-off flows around the emission flow keep the velocity profile of the flow under control.

In one embodiment, the ions are removed by placing very thin metal plates, in some of which there is a voltage, in the flow channel. Ions are permitted to enter the measurement chamber from a single gap. In this case, the emission gap is in the centre part of the channel, or not completely at the side. The location of the emission gap in the centre channel is advantageous, because the ions are distributed relative to the flow and the greatest ion density per unit of time is in the centre of the channel. The ions are allowed through the centre-most (or otherwise selected) gap by setting them to the same potential. The ions are colleted away from elsewhere by means of a suitable barrier field. Sufficiently thin plates do not disturb the flow, but instead equalize the flow resistance of the channel suitable, in such a way that the flow travels through each gap. In a preferred construction, the flow-guiding plates can have mutually differing dimensions, for control of the flow distribution.

The features of portable size-class second-order aspiration IMS according to the invention can be summarized as follows:

Ions are produced over the entire height of the flow channel, for example, by means of a radioactive source. Ions are permitted to enter the measuring chamber from a limited area, by filtering ions from elsewhere out by means of a plate structure dividing the flow channel, preferably from the maximum point of the velocity distribution of the flow. Here, the greater ion density (per unit of time) of the centre part of the flow channel is exploited, by permitting the ions coming from the centre part to enter the mobility measuring chamber. The ions can be guided by means of an electric field before the emission-plate structure, for example, by increasing the ion density in the centre part of the channel by means of the electric field. The emission-plate structure also acts as a shade, preventing direct ionizing radiation from entering the measuring chamber. The construction permits compact measuring. The construction can be exploited in order to implement DMS/FAIMS-type measurement. The construction can be combined with the so-called SWEEP-type measurement, when the desired part of the mobility distribution is picked out of the second-order produced ion flow.

BRIEF DESCRIPTION OF FIGURES

In the following, the invention is described with the aid of examples and with reference to the accompanying drawings, in which FIG. 10 shows an axonometric view and cross-section of a second practical implementation of an aspiration IMS cell, and FIG. 11 shows a cross-section, more simplified than the previous, of a third practical implementation of an aspiration IMS cell.

DETAILED DESCRIPTION

Figure 3A:
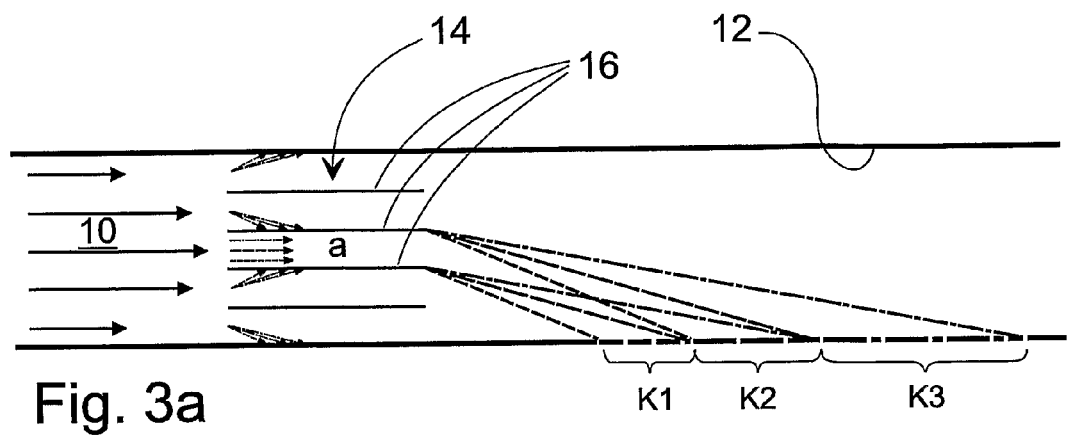
FIG. 3a shows a schematic diagram of another second-order aspiration IMS cell.

The operation of the position-separating second-order aspiration IMS is shown as a schematic diagram in FIG. 3a. An ionized gas flow 10 is led into the measuring channel 12, by means of which a typically parabolic velocity profile arises in the channel. From the point of view of the actual measurement, the central component is a position-separating cell, in which ions with different mobilities are collected into different positions, which are referred to by the marks K1, K2, and K3. The air flow comes with a parabolic profile, in such a way that in the centre the flow is greatest. Due to the flow profile, more ions arrive at the centre in a unit of time than arrive at the edges. The ions are collected away from the edges with the aid of a pre-filter 14. This comprises thin metal plates 16, in the two outermost of which collection voltages are set. The channels with an electric field are referred to as shut-off channels, as they remove ions. The shut-off channels have scarcely any effect on the actual gas flow. The centre-most plates are earthed, or set to the same mutual potential, in such a way that there is no electric field between them and the ions pass through them, so that an emission channel a is formed between these plates. By means of the construction, the different mobilities are collected precisely in different positions. In a preferred construction, the cross-sectional surface area of the centre-most channel is small relative to the total cross-sectional surface area and there are numerous emission channels. For simplicity, only the number of gaps needed to illustrate the idea are drawn in the figure.

Figure 3B:
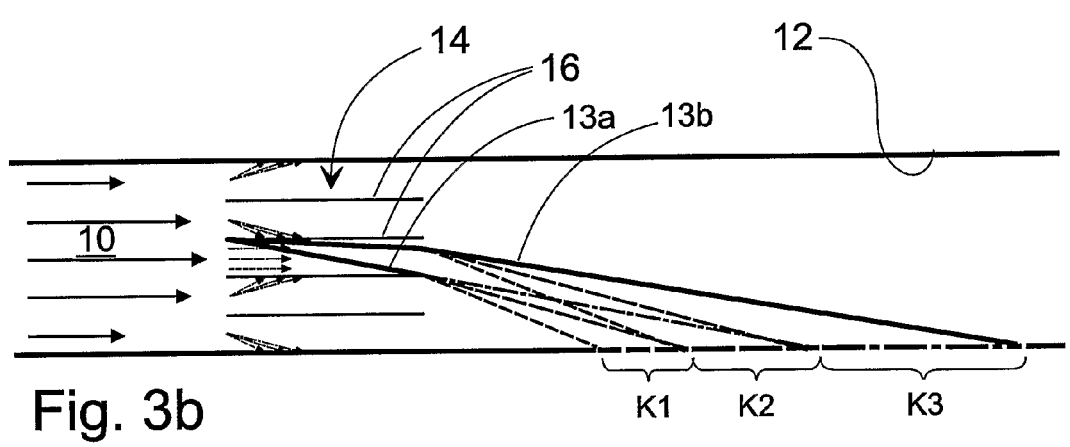
FIG. 3b shows a variation of the embodiment of FIG. 3a, FIG. 4 shows one alternative for implementing the barrier-plate structure of the pre-filter.

According to FIG. 3b, the emission channel can be adapted as a filter, if, differing from the above, there is indeed either a static or a slowly changing (scanning) small electric field. In this figures, the boundaries 13a and 13b are shown:

Boundary line 13a: mobility is limited by a DMS or DC emission field, ions with a greater mobility will not pass through.

Boundary line 13b: ions with a lower mobility emitted from a DMS or DC field, which pass through and proceed to the measuring area for separation.

The emission channel can also be used as a filter in two ways:

1) By setting a voltage (field) in the emission channel, it is possible, with the aid of the emission channel, to limit the entry to the measuring channel of high mobilities. The voltage of the emission channel determines the mobility, above which there is no entry to the measurement. By altering this voltage in steps, the measurement accuracy can be significantly improved by selecting a suitable emission window.

2) By using the emission channel as a DMS filter, only these ions can be allowed to enter the measurement, which pass through the asymmetrical electric field, which is relative to each of the compensation voltage, the time and field strength of the DMS filter.

The aforementioned methods can also be alternated, because alternation can be utilized to increase the measurement speed.

Figure 4:
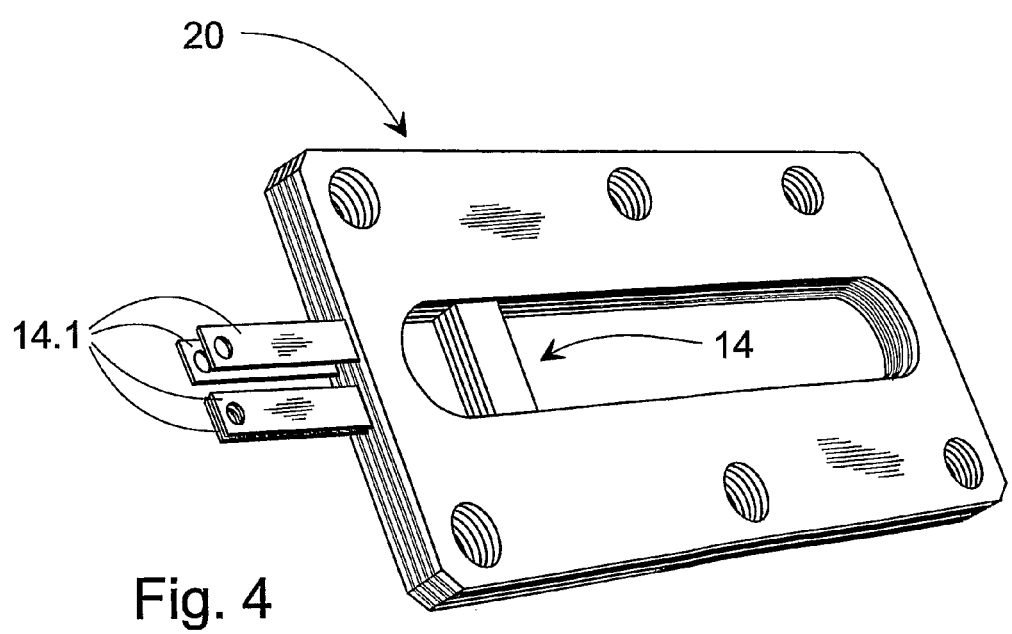

FIG. 4 shows one alternative way to implement the barrier-plate construction of the pre-filter 14. The body of the sensor is marked with the reference number 20. In the implementation of FIG. 4, the ions are ionized elsewhere and the ionized air is brought to the flow channel immediately before the barrier plates (from the left). In the figure, the strips 14.1 on the left relative to the voltage field in this prototype implementation. In a mass-manufactured construction, the plates are connected to the voltage source through assembly holes or other separate connection points.

Figure 1:
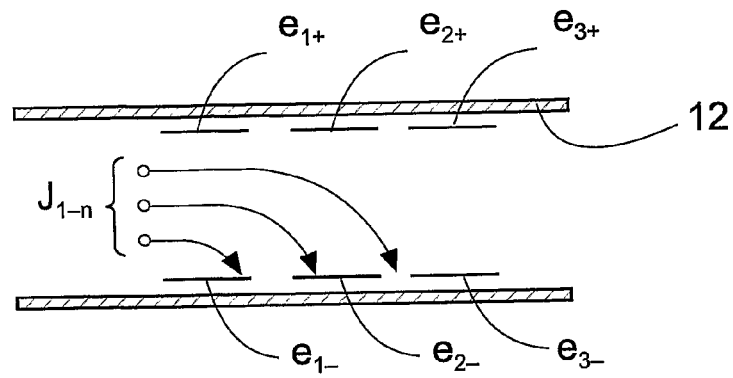
FIG. 1 shows the manner of implementing a traditional aspiration cell.
Figure 2:
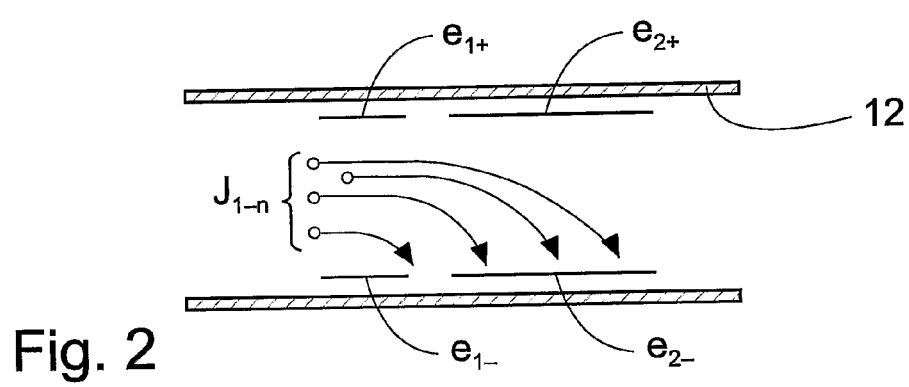
FIG. 2 shows the construction of a so-called SWEEP cell.
Figure 5:
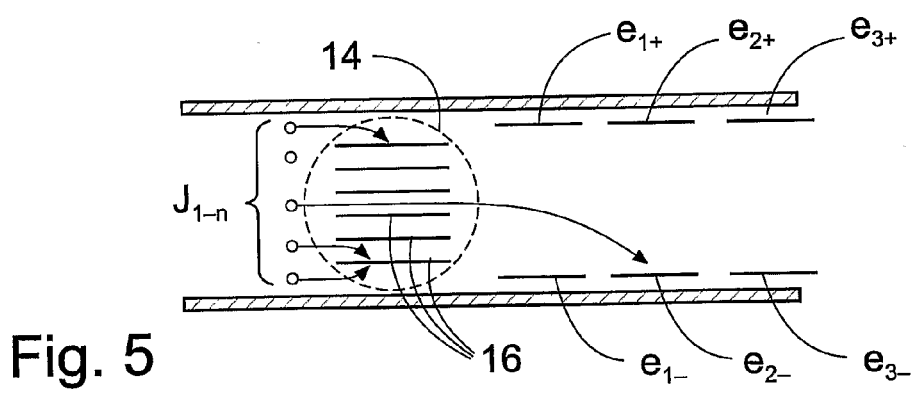
FIG. 5 shows the construction of another second-order aspiration IMS.

FIG. 5 shows schematically a second-order construction in principle. The ions $J_{1-n}$ arrive at the pre-filter from the entire area of the flow channel, but leave the pre-filter 14 only from the centre. For reasons of simplicity, only three measuring channels $e_1$-$e_3$, i.e. measuring strips, are drawn in the figure, in reality there can be more of them.

Figure 6:
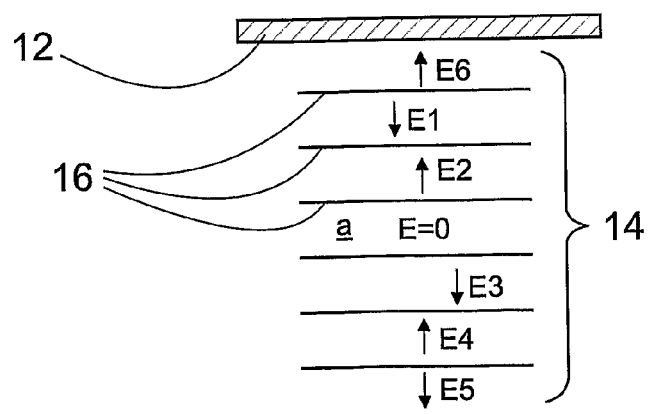
FIG. 6 shows the schematic construction of a pre-filter.

The construction in principle of the pre-filter can be seen in FIG. 6, in which E signifies generally an electric field while the numbers next to the letter refer to the fact that in a practical arrangement each field can have a different magnitude. Though in an optimal situation the centre-most field (E=0) is indeed arranged in such a way that the field strength in it is zero, or a varying field is used for the flow channel in question. In this case, the emission channel is marked with the reference 'a'. The use of other fields relates to the removal of ions, the use of a multi-channel solution, for its part, seeks to equalize the channel flow by making a unified flow resistance over the entire channel.

Figure 7:
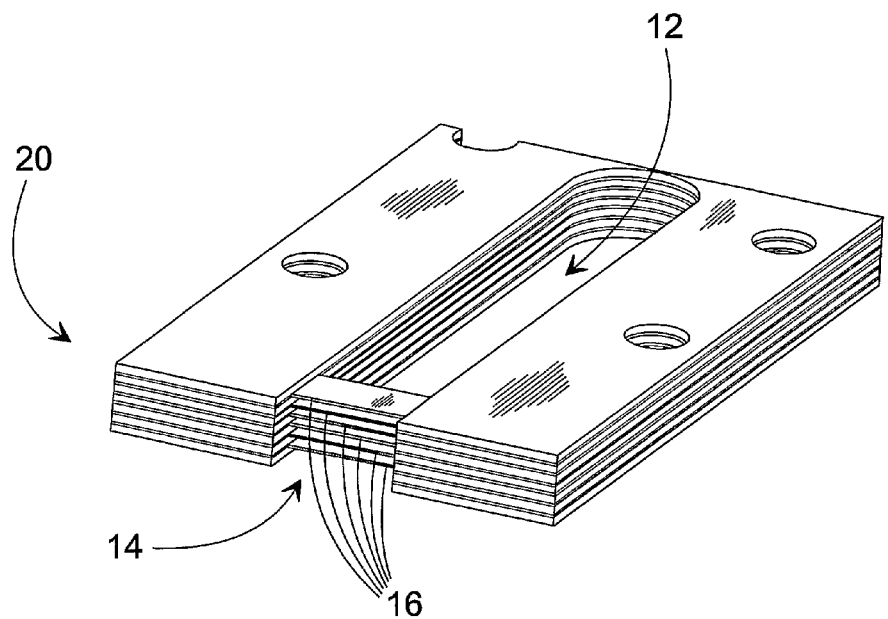
FIG. 7 shows a cross-sectional view of the flow channel, before the pre-filter.

FIG. 7 shows an insulating pack 20 and a cross-section of the flow channel 12 formed inside it, cut off before the pre-filter 14. The gas flow enters from the left-hand side in the figure and travels in the channel through the pre-filter 14 and exits from an opening (not shown) arranged at the end of the flow channel. The measuring plates above and below the insulating pack 20, which close the construction, are not drawn in FIG. 7. The figure shows the overall construction of the system, which consists of alternating insulating and field plates.

The ions can be measured position-independently using a constant electric field, or a varying electric field, from one or more locations. Both are described in publications and in patents. The second-order solution described above can be further developed by producing ions as close as possible to the measurement and guiding the ions by an electric field before collection, or mechanically by means of plates intended for flow control. These measures are intended to maximize the flow signal brought by the ions being measured.

Figure 8:
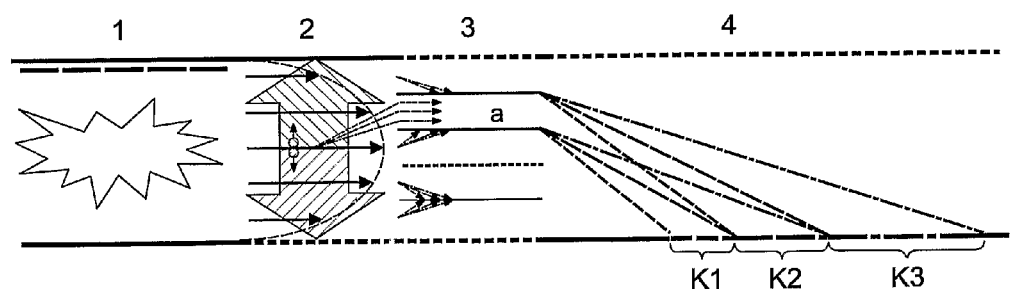
FIG. 8 shows a schematic diagram of the previous, slightly modified second-order solution.

In FIG. 8, there is a schematic diagram of a second-order solution slightly modified from the preceding one. In this embodiment, ions with differing polarity are guided separately from each other by an electric field. The intention is to slow the recombination of the ions and to increase the number of ions reaching measurement and through that the electrical current being measured. Because the separation of polarity moves the arriving ions from the centre part, the emission gap is located accordingly.

Above is a schematic diagram of a electromechanical second-order implementation. The height of the flow channel 12 can be, for example, 5 mm. The radiation source can then be located in the flow channel (stage 1—ionization area). In the figure, the broken line inside the tube shows the radiation source schematically. Immediately after formation, the different polarities are separated from each other by an electric field (stage 2—pre-separation of the ions according to polarity). The separation of the polarities moves the measuring polarity slightly away from the centre part. The intention is to exploit the high velocity of the centre part of the flow channel over a wide area.

Implementing ionization as close as possible to the measurement of mobility maximizes the number of ions being measured. The separation of the polarities from each other reduces the recombination speed and this probably has the effect of clearly increasing the number of ions. Besides its main task, the ion pre-filter (stage 3—ion barrier fields and emission channel a) also acts as a shade for the alpha particles of the radiation source, i.e. it prevents the alpha particles from entering the ion-mobility measuring chamber (stage 4—measurement of mobility).

In addition to the above manners of implementation, a second-order construction can also be implemented as a so-called DMS construction, in which a filter intended to create the second order is utilized, in order to create an asymmetric high-frequency field with a great strength. The DMS measurement principle is, as such, known, but the way of implementing it in a second-order manner is new.

Figure 9:
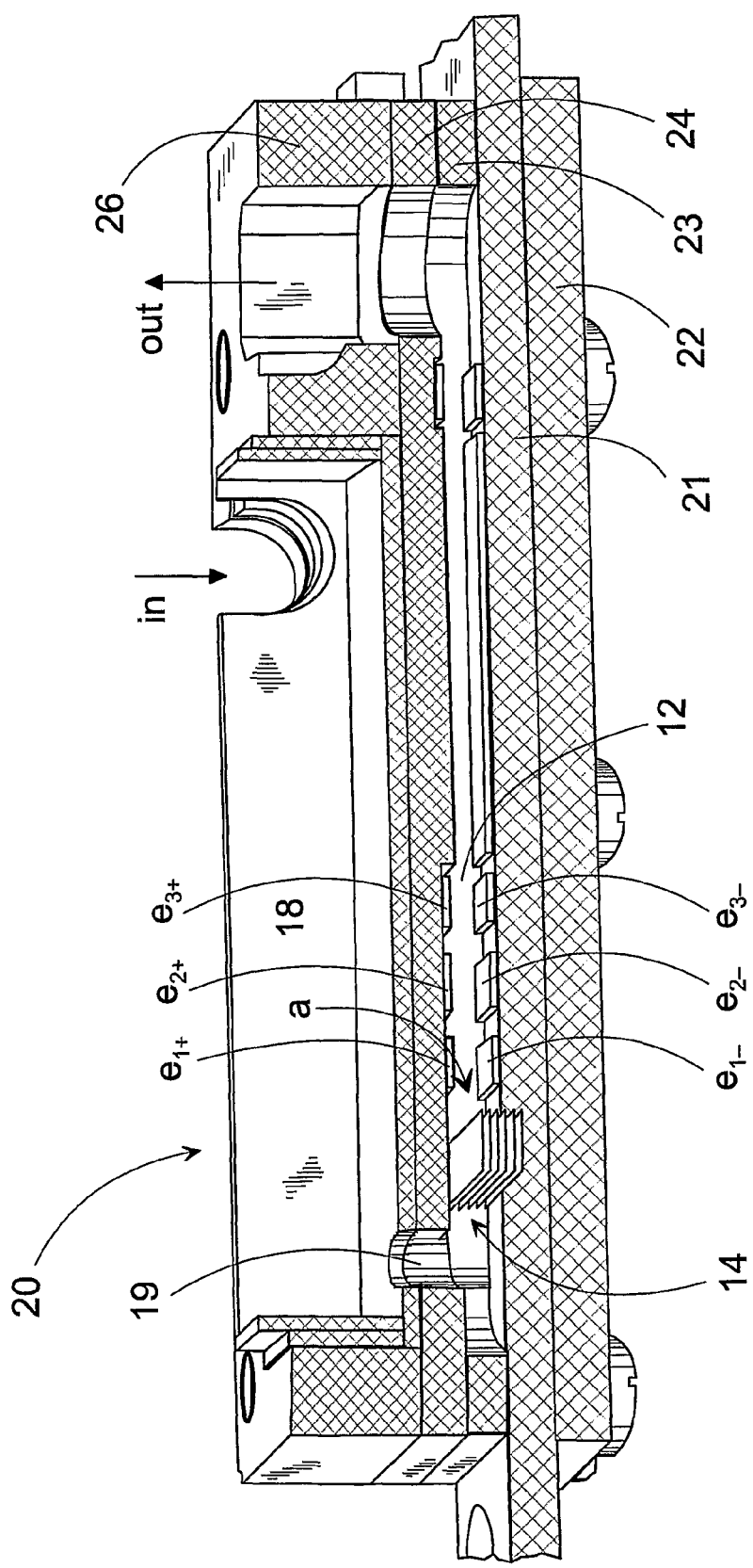
FIG. 9 shows an axonometric view and cross-section of a practical implementation of an aspiration IMS cell.

A more detailed view of the sensor component 20 of the ion-mobility spectrometer is shown in FIG. 9, in which the sensor component is cross-sectioned longitudinally at the measuring channel 12 and the ion chamber 18 above is cross-sectioned horizontally.

In this case, the bottom measuring plate 21 is part of a larger circuit board, in which there is the rest of the electronics of the device. The sensor component comprises a layered construction, in which the lowest is a support plate 22, with on top of it in order are: a lower measuring plate 21, a channel plate 23, an upper measuring plate 24, and a thicker connector plate 26.

The sample gas is brought from the connection 'in' to the ionization chamber 18, in which there is the chosen radiation source 8 (not shown). The ionized sample gas is led through an intermediate connection 19 to an elongated measuring chamber 12, the operation of which will be explained later. From the measuring chamber 12, the sample gas is removed to the connection 'out'—either to the surrounding air, or, in closed sampling, back to its starting point.

In the known manner, in the measuring chamber 12 there are measuring strips ($e_1$, $e_2$, $e_3$) each as an electrode pair (e.g., $e_{1+}$ and $e_{1-}$), the voltage of which is kept constant and the current in which is measured.

In this figure, the ion pre-filter 14 is not shown in cross-section and thus protrudes from the section plane of the rest of the construction. At the same time, it gives some idea of the width of the measuring chamber 12. As described above, the pre-filter 14 comprises thin metal plates, which are connected to the selected potentials. The emission-channel plates, i.e. generally the centre-most plates, are earthed. The voltage is led to the plates from the other side (not shown).

A second, more simplified embodiment of the ion-mobility spectrometer is shown in FIG. 10, in which the sensor component is cross-sectioned as in FIG. 9. The same reference numbers as above are used for components that are functionally similar. The similar components are:

ion chamber 18 equipped with a connection 'in',
measuring chamber 12,
intermediate connection 19 connecting the ion chamber 18 to the measuring chamber 12,
'out' connection at the end of the measuring chamber,
construction assembled from plates, comprising plates 22, 21, 23, 24, 25, and 26, and, in addition, as new plates 22a and 24a-24d.

The layered construction is similar to the previous one, but the plates are of equal thickness and, instead of removing part of the thickness of the plates, thinner separate plates are used. The pre-filter 14 is formed in such a way that, at a selected point in the plates 21 and 24, there are necks 16' across the measuring chamber. In these necks, there are conductors on the surface of the plates, corresponding to the separate plates 16 in FIGS. 7 and 9. The electrodes are thus part of each circuit board. Part channels are formed between the necks 16', of which in this case there are three. The centre-most one is the emission channel (a) while the other two are shut-off channels. The electrodes creating the static zero field of the emission channel are either inside the emission channel, or outside the insulation. The electrodes of the emission channel can be separate or common in pairs on each side with the nearest electrodes of the shut-off channel.

The layered construction can naturally be formed in many other ways. The central features of the construction are the channel spaces and the electrodes. The measuring chamber 12 narrows after the pre-filter 14, to become a channel 12' that is even narrower than the emission channel a. In the channel 12', there are separator electrodes as above (not shown) and its height is about 20% (generally 10-30%) of the height of the pre-filter, the width remaining the same. This construction has been proven to be surprisingly functional and stable. The emission flow narrows between the shut-off flows coming from the edges, which together become larger while not mixing with the measuring channel 12'. The ions can then be guided precisely into the narrow part at the smaller cross-section of the measuring channel and distance separation is obtained precisely. The separation works well at a low voltage, because the transverse distance is small (0.2-1 mm, preferably 0.4-0.7 mm). Generally, using one or two shut-off channels the emission flow containing the ions can be guided precisely to the selected point of the smaller cross-section.

FIG. 11 shows in a simplified form yet another embodiment. In the measuring chamber of even thickness there is a pre-filter, in which the length of the shut-off channel plates 16a is in inverse accordance with the velocity profile, i.e. the length of the plates diminishes towards the emission channel. The plates of the emission channel a are, in addition, slightly protruding relative to the rest of the plate pack. This is used to direct the shape of the electric field and the flow profile. Separation takes place in the same way as describe above.

In the embodiment described above, 1-3 litres per minute, preferably about 2 l/min is typically used as the flow velocity of the of the sample gas.

The invention claimed is:

1. Method for measuring gaseous substances, which method comprises the stages:
    ionization of the sample gas in a gas flow,
    leading of the ionized gas flow through an elongated ion-mobility measuring chamber,
    separation of ions with differing ion mobilities in the measuring chamber with the aid of a transverse electric field and at least one measurement-electrode pair arranged on the wall of the measuring chamber,
characterized in that
    at a chosen distance in the flow direction before the measuring electrodes, the gas flow is divided into at least two part-flows for the pre-filtering of the ions, in which
    one of the part-flows at the chosen point is referred to as the emission flow, the other part-flows being referred to as shut-off flows, and
    when the ions are filtered out of the said ionized gas flow from each of the shut-off flows with the aid of a static electric field relative to the mobility of the ions, and
    at least the selected ions in the emission flow are permitted to enter the separation after the said pre-filtering, with the aid of a 0-field arranged in the emission flow.

2. Method according to claim 1, characterized in that there are at least three part-flows and the said emission flow is at essentially the maximum point of the velocity distribution of the gas flow.

3. Method according to claim 1, characterized in that the part flows are created by means of part channels, the lengths of which diminish from the edges towards the emission flow.

4. Method according to claim 1, characterized in that, after the pre-filtering, the gas flow is directed to a substantially smaller cross-section, in which the emission flow containing the ions is guided by at least one non-ionized shut-off flow to a precisely defined point in the said smaller cross-section.

5. Method according to any of claim 1, characterized in that, before the pre-filtering, the ions are separated from each other on the basis of different polarities.

6. Ion-mobility spectrometer for measuring gaseous substances, in which the ion-mobility spectrometer includes
    a measuring chamber,
    means for creating a gas flow and guiding it through the measuring chamber,
    means for ionizing the gas flow before the measuring chamber,
    means for creating a transverse measuring electrical field over a chosen length of the measuring chamber and at least one measuring-electrode pair on the wall of the measuring chamber,
    means for measuring the ion flow from each measuring-electrode pair, characterized in that the measuring chamber includes
    a pre-filter arranged in the flow direction before the measuring-electrode pairs for dividing the measuring chamber in the cross-section into at least two separate parallel part channels in order to create part flows, one part channel being the emission channel, the others being shut-off channels, and
    means for creating a static electric field relating to the mobility of the ions, and collection electrodes in each shut-off channel for collecting away the part flows of these part channels,
    one electrically passive part channel forming the said emission channel at a chosen point of the cross-section, permitting the ions to travel as undisturbedly as possible through it.

7. Ion-mobility spectrometer according to claim 6, characterized in that the selected part channels are at least three, the emission channel being located between the shut-off channels.

8. Ion-mobility spectrometer according to claim 6, characterized in that the part channels are formed using several thin metal plates, which divide the measuring chamber into narrow parts over a selected length.

9. Ion-mobility spectrometer according to claim 6, characterized in that the pre-filter comprises 3-11, part channels.

10. Ion-mobility spectrometer according to claim 6, which is assembled from a plate pack formed of plates on top of each other, in which plates openings are formed on top of each other in order to create the measuring chamber and other channel spaces, characterized in that the part channels of the pre-filter are formed by necks penetrating the measuring chamber in selected plates, there being openings at a corresponding location in the plates between them.

11. Ion-mobility spectrometer according to any of claim 6, characterized in that it includes additional electrodes with a voltage source, located before the pre-filter, for separating from each other ions with different polarities, by means of an electric field.

12. Ion-mobility spectrometer according to claim 11, characterized in that the collector electrodes of the pre-filter are each part of a circuit board, from which the said plate are made.

* * * * *